(12) United States Patent
Heidl et al.

(10) Patent No.: US 8,541,361 B2
(45) Date of Patent: Sep. 24, 2013

(54) COMPOSITION

(75) Inventors: Marc Heidl, Lörrach (DE); Roman Wille, Basel (CH); Hugo Ziegler, Witterswil (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/264,059

(22) PCT Filed: Apr. 23, 2010

(86) PCT No.: PCT/IB2010/001011
§ 371 (c)(1),
(2), (4) Date: Feb. 1, 2012

(87) PCT Pub. No.: WO2010/122423
PCT Pub. Date: Oct. 28, 2010

(65) Prior Publication Data
US 2012/0129786 A1    May 24, 2012

Related U.S. Application Data

(60) Provisional application No. 61/202,947, filed on Apr. 22, 2009.

(30) Foreign Application Priority Data

Apr. 22, 2009  (EP) .................................. 09158422

(51) Int. Cl.
*A61K 38/00* (2006.01)
*A61P 17/00* (2006.01)

(52) U.S. Cl.
USPC ........................... 514/1.1; 514/18.6; 514/18.8

(58) Field of Classification Search
None
See application file for complete search history.

(56) References Cited

U.S. PATENT DOCUMENTS

| | | | |
|---|---|---|---|
| 4,233,211 A * | 11/1980 | Ohtomo et al. | 530/353 |
| 7,863,417 B2 * | 1/2011 | Ziegler et al. | 530/331 |
| 2006/0104931 A1 * | 5/2006 | Fukutome et al. | 424/70.13 |
| 2008/0095732 A1 | 4/2008 | Osborne | |

FOREIGN PATENT DOCUMENTS

| | | |
|---|---|---|
| DE | 10 2005 06317 | 9/2006 |
| WO | WO 2004/099237 | * 11/2004 |
| WO | WO2004099237 | * 11/2004 |
| WO | WO 2007/068998 | 6/2007 |

OTHER PUBLICATIONS

International Search Report for PCT/IB2010/001011, mailed Dec. 8, 2010.

* cited by examiner

*Primary Examiner* — Cecilia J Tsang
*Assistant Examiner* — Sergio Coffa
(74) *Attorney, Agent, or Firm* — Nixon & Vanderhye P.C.

(57) ABSTRACT

The present invention relates to compositions comprising a peptide with 2-12 amino acids substituted with a lipophilic moiety and a water soluble salt of an alkali, earth alkaline metal or transition metal. Furthermore, the invention relates to a container comprising such compositions. Additionally, the invention relates to the use of a water soluble salt of an alkali, earth alkaline metal or transition metal for reducing the adhesion of a peptide with 2-12 amino acids substituted with a lipophilic moiety to a surface.

27 Claims, No Drawings ial-Peptide™ (available at DSM Nutritional Products Branch Pentapharm; Matrixyl® (INCI-name: Palmitoyl pentapeptide-4) at Sederma.

```
                             SEQUENCE LISTING

<160> NUMBER OF SEQ IDS NOS: 12

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-His
<220> FEATURE:
<221> NAME/KEY: MOD_RES
<222> LOCATION: (2)..(2)
<223> OTHER INFORMATION: D-Phe
<220> FEATURE:
<223> OTHER INFORMATION: C-term NH2

<400> SEQUENCE: 1

His Phe Arg
1

<210> SEQ ID NO 2
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Lys

<400> SEQUENCE: 2

Lys Val Lys
1

<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Elaidyl-Lys

<400> SEQUENCE: 3

Lys Phe Lys
1

<210> SEQ ID NO 4
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hexanoyl-Arg
<220> FEATURE:
<221> NAME/KEY: MOD_RES
<222> LOCATION: (3)..(3)
<223> OTHER INFORMATION: Nle
<220> FEATURE:
<223> OTHER INFORMATION: C-term NH2

<400> SEQUENCE: 4

Arg Ala Leu
1

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Lys
<220> FEATURE:
<221> NAME/KEY: MOD_RES
<222> LOCATION: (3)..(3)
<223> OTHER INFORMATION: 2,4-diaminobutyroyl

<400> SEQUENCE: 5

Lys Val Xaa
1
```

```
-continued

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Lys
<220> FEATURE:
<221> NAME/KEY: MOD_RES
<222> LOCATION: (3)..(3)
<223> OTHER INFORMATION: 2,4-diaminobutyroyl

<400> SEQUENCE: 6

Lys Val Xaa Thr
1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Lys

<400> SEQUENCE: 7

Lys Thr Thr Lys Ser
1               5

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Gly

<400> SEQUENCE: 8

Gly His Lys
1

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Gly

<400> SEQUENCE: 9

Gly Lys His
1

<210> SEQ ID NO 10
<211> LENGTH: 4
<212> TYPE: PRT
<213> ORGANISM: Artificial Sequence
```

```
-continued

<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Gly

<400> SEQUENCE: 10

Gly Gln Pro Arg
1

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Val

<400> SEQUENCE: 11

Val Gly Val Ala Pro Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Palmitoyl-Ala

<400> SEQUENCE: 12

Ala Glu Asp Glu Pro Leu Leu Met Glu
1               5
```

COMPOSITION

This application is the U.S. national phase of International Application No. PCT/IB2010/001011, filed 23 Apr. 2010, which designated the U.S. and claims priority to EP Application No. 09158422.7, filed 22 Apr. 2009; and claims the benefit of U.S. Provisional Application No. 61/202,947, filed 22 Apr. 2009, the entire contents of each of which are hereby incorporated by reference.

The present invention relates to compositions comprising a peptide with 2-12 amino acids substituted with a lipophilic moiety and a water soluble salt of an alkali, earth alkaline metal or transition metal. Furthermore, the invention relates to a container comprising such compositions. Additionally, the invention relates to the use of a water soluble salt of an alkali, earth alkaline metal or transition metal for reducing the adhesion of a peptide with 2-12 amino acids substituted with a lipophilic moiety to a surface.

Peptides substituted with a lipophilic moiety such as Palmitoyl pentapeptides (e.g. Matrixyl® (INCI-name: Palmitoyl pentapeptide-4) and Palmitoyl tripeptides such as e.g. SYN®-Coll (INCI-name: Palmitoyl tripeptide-3) or SYN®-Tacks (INCI-name: Glycerin, Palmitoyl Dipeptide-5 Diaminobutyloyl Hydroxythreonine, Palmitoyl Dipeptide-6 Diaminohydroxybutyrate) are widely used in cosmetic applications. However, the commercially available stock solutions comprising the peptides show a significant loss of the active ingredient over time which is highly unwanted. This loss was for a long time unexplainable as no degradation products are detectable.

It has now been found that this loss is due to an unwanted adhesion of the peptides substituted with a lipophilic moiety to the surface of the container. Furthermore, it has been found that this loss can be significantly reduced respectively completely be prevented by the addition of a water soluble salt of an alkali, earth alkaline metal or transition metal.

Thus, in one embodiment the invention relates to a composition comprising a peptide with 2-12 amino acids substituted with a lipophilic moiety and a water soluble salt of an alkali, earth alkaline metal or transition metal.

In another embodiment, the composition according to the invention further comprises at least one water-soluble polyol containing 2 to 10 carbon atoms and 2 to 7 hydroxyl groups and water.

In a further embodiment the invention relates to a composition comprising
(i) 0.001-12.5 wt.-%, particularly 0.01-2 wt.-%, most particularly 0.1-0.5 wt.-% of a peptide with 2-12 amino acids substituted with a lipophilic moiety
(ii) 0.00001-2 wt.-%, particularly 0.01-0.5 wt.-%, most particularly 0.05-0.01 wt.-% of a water soluble salt of an alkali, earth alkaline metal or transition metal
(iii) 10-95 wt.-%, particularly 40-80 wt.-%, most particularly 40-70 wt.-% of at least one water-soluble polyol containing 2 to 10 carbon atoms and 2 to 7 hydroxyl groups and
(iv) 10-90 wt.-%, particularly 20-50 wt.-%, most particularly 25-35 wt.-% of water whereas the total amount of the ingredients sums up to 100 wt.-%.

Preferably, the molar ratio of the peptide to the water soluble salt of an alkali, earth alkaline metal or transition metal is selected in the range of 10:1 and 1:50, preferably in the range of 2:1 to 1:10, most preferably in the range of 1:1 to 1:4.

The compositions according to the invention may further contain tensides and/or thickeners. Suitable tensides appropriate for cosmetic applications are well known to a person skilled in the art and include in particular non ionic tensides such as e.g. Polysorbate-20. Suitable thickeners appropriate for cosmetic applications are also well known to a person skilled in the art and include e.g. polyacrylic acids (Carbomers).

In another embodiment the invention relates to the use of a water soluble salt of an alkali, earth alkaline metal or transition metal to reduce the adhesion of a peptide with 2-12 amino acids substituted with a lipophilic moiety to a surface.

The term peptide with 2-12 amino acids substituted with a lipophilic moiety refers to a peptide wherein a lipophilic moiety is connected thereto via an ester, amide, N-alkyl, N-alkenyl, sulfonyl, urethane (oxocarbonyl substituted amino acid), urea (aminocarbonyl substituted amino acid) linkage. In particular, the term peptide with 2-12 amino acids substituted with a lipophilic moiety refers to N-acyl-derivatives thereof such as most in particular to the N-palmitoyl or N-tetradecylcarbonyl derivatives.

The lipophilic moiety is in particular an alkyl moiety wherein the term alkyl refers to saturated or unsaturated linear or branched chain hydrocarbon groups containing 5 to 35, preferably 8 to 20 carbon atoms, such as e.g. pentyl, neopentyl, hexyl, 2-ethyl-hexyl, octyl, nonyl, decyl, tetradecyl, hexadecyl or octadecyl residue. Particularly the lipophilic moiety is a linear tetradecyl or hexadecyl residue.

Particularly, the peptides substituted with a lipophilic moiety are di- to nonapeptides such as particularly Palm-β-Ala-His-OH, Oleyl-Gly-Gly-OH, Palm-His-D-Phe-Arg-NH$_2$ (SEQ ID NO:1), Acetyl-Tyr-Arg-OCetyl, Palm-Lys-Val-Lys-OH (SEQ ID NO:2), Elaidyl-Lys-Phe-Lys-OH (SEQ ID NO:3), Hexanoyl-Arg-Ala-Nle-NH$_2$ SEQ ID NO:4), Palm-Lys-Val-Dab-OH (SEQ ID NO:5), Palm-Lys-Val-Dab-Thr-OH (SEQ ID NO:6), C$_{14}$H$_{29}$-NH-CO-Dab-Val-Dab-OH, Palm-Lys-Thr-Thr-Lys-Ser (SEQ ID NO:7), Palm-Gly-His-Lys-OH (SEQ ID NO:8), Palm-Gly-Lys-His-OH (SEQ ID NO:9), Palm-Gly-Gln-Pro-Arg-OH (SEQ ID NO:10), Palm-Val-Gly-Val-Ala-Pro-Gly-OH (SEQ ID NO:11), Palm-Ala-Glu-Asp-Glu-Pro-Leu-Leu-Met-Glu-OH (SEQ ID NO:12), more in particular Palm-Lys-Val-Lys-OH (SEQ ID NO:2), Palm-Lys-Val-Dab-OH (SEQ ID NO:5), Palm-Lys-Val-Dab-Thr-OH (SEQ ID NO:6), C$_{14}$H$_{29}$-NH-CO-Dab-Val-Dab-OH wherein Palm means palmitoyl and Dab means 2,4-diaminobutyroyl.

According to a particular embodiment of the invention, the peptides substituted with a lipophilic moiety are acid addition salts such as chloride, acetate or trifluoroacetate salts, in particular trifluoroacetate salts or salts formed by the addition of a base such as alkali or earth alkaline salts, in particular lithium, sodium, potassium, magnesium or calcium salts.

Suitable peptides substituted with a lipophilic moiety are known and e.g. described in WO 2004/099237 WO 2007/124770, WO 2000/15188, WO 2000/40611, WO 2000/43417, WO 01/43701, US 2002197219, FR 2786693, WO 2005/048968, FR 2810323, WO 2005/116067, WO 99/48470, WO 2009/010356 and Int. J. Cosmetic Science 22(3), 207-218 (2000).

Commercially available dipeptides include e.g. Sensicalmine™ (INCI-name: Acetyl-Dipeptide-1 Cetyl Ester) available at Sederma.

Commercially available tri- and tetrapeptides include e.g. SYN®-Coll (INCI-name: Palmitoyl tripeptide-3) or SYN-®Tacks (INCI-name: Glycerin, Palmitoyl Dipeptide-5 Diaminobutyloyl Hydroxythreonine, Palmitoyl Dipeptide-6 Diaminohydroxybutyrate) available at DSM Nutritional Products Branch Pentapharm; or BIOPEPTIDE CL (INCI-name: Palmitoyl Tripeptide-1), RIGIN™ (INCI-name: Palmitoyl-Tetrapeptide-3) or EYELISS™ (INCI-name: Palmitoyl-Tetrapeptide-7) available at Sederma; or Neutrazen™ (INCI-name: Palmitoyl tripeptide-8) available at IEB (Institut Européen de Biologie Cellulaire).

Commercially available pentapeptides include e.g. Matrixyl® (INCI-name: Palmitoyl pentapeptide-4) available at Sederma.

Commercially available hexapeptides include e.g. BIO-PEPTIDE EL (INCI-name: Palmitoyl Oligopeptide) available at Sederma.

Any water soluble salt of a alkali, earth alkaline metal or transition metal or mixtures thereof with cosmetically acceptable anions can be used in the compositions according to the invention such as the chlorides, bromides, acetates, trifluoroacetates, sulfates, lactates, succinates or phosphates. Preferably the alkali, earth alkaline metal or transition metal is selected from Mg, Ca, Zn, Li and/or Na salts. Particularly $MgCl_2$, $CaCl_2$, $ZnCl_2$, LiCl and/or NaCl, more in particular $MgCl_2$ is used.

The water-soluble polyol containing 2 to 10 carbon atoms and 2 to 7 hydroxyl groups is in particular selected from ethylene glycol, 1,2-propylene glycol, 1,4-butylene glycol, glycerine, erythrit (meso-1,2,3,4-Butantetrol), sorbit, mannit, methylglucoside, diglycerine, triglycerine and/or pentaerythrit. Particularly, the polyol is glycerine, 1,2-propylene glycol and/or 1,4-butylene glycol The compositions according to the invention particularly can be in the form of a solution, a viscous liquid or in the form of a gel.

The invention further relates to a container comprising the composition according to the invention. Suitable containers include any containers suitable for packaging and transport of the compositions according to the invention. Such container can be made of glass, polyethylene, polystyrene, polylactic acid, polyethyleneterephthalat or polypropylene without being limited thereto. Suitable containers are well known and can easily be chosen by a person skilled in the art such as polyethylene canisters with a volume of e.g. 1 kg or 10 kg, glass container with a volume of e.g. 50 ml, 1l, 2.5l or polyethylene canister with a volume of e.g. 100 ml.

The compositions according to the invention can be incorporated into topical preparations useful for improving skin appearance and physiology such as e.g. reducing fine lines, wrinkles and other symptoms associated with aged or photodamaged skin, treatment of stretch marks or tightening, firming and/or moisturizing skin.

Thus, the invention also relates to a topical preparation comprising a composition according to the invention and a cosmetically acceptable carrier.

The term topical preparation as used herein refers in particular to cosmetic compositions that can be topically applied to mammalian keratinous tissue such as e.g. human skin or hair (including eyelashes, the eyebrows) or the nails, particularly human skin.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), 4$^{th}$ edition, 1992.

The term cosmetically acceptable carrier refers to all carriers and/or excipients and/or diluents conventionally used in topical compositions.

Preferably, the topical compositions are in the form of a suspension or dispersion in solvents or fatty substances, or alternatively in the form of an emulsion or micro emulsion (in particular of O/W- or W/O-type), PIT-emulsion, multiple emulsion (e.g. O/W/O- or W/O/W-type), pickering emulsion, hydrogel, alcoholic gel, lipogel, one- or multiphase solution or vesicular dispersion or other usual forms, which can also be applied by pens, as masks or as sprays. If the topical composition is or comprises an emulsion it can also contain one or more anionic, nonionic, cationic or amphoteric surfactant(s).

Preferred topical compositions are skin care compositions, and functional compositions.

Topical preparations in accordance with the invention can be in the form of a liquid, lotion, a thickened lotion, a gel, a cream, a milk, an ointment, a paste, a powder, a make-up, or a solid tube stick and can be optionally be packaged as an aerosol and can be provided in the form of a mousse such as a aerosol mousse, a foam or a spray foam, a spray, a stick, a plaster, a cleanser, a soap, a wipe or a lyophilizate (such as the Pentapharm Dual Vial system).

The topical preparations according to the invention are preferably formulated as an oil-in-water or water-in-oil emulsion, water-in-silicone or silicone-in-water emulsion or as an aqueous serum or aqueous gel in particular in as an oil-in water emulsion (O/W emulsion).

The topical preparations according to the invention have a pH in the range of 3-10, preferably in the range of pH of 4-8, most preferred in the range of pH 4-6.

In accordance with the present invention, the topical preparation may optionally comprise further ingredients such as ingredients for skin lightening; tanning prevention; treatment of hyperpigmentation; preventing or reducing acne, wrinkles, lines, atrophy and/or inflammation; as well as topical anesthetics; antimicrobial and/or antifungal agents; chelators and/or sequestrants; anti-cellulites and slimming (e.g. phytanic acid), firming, moisturizing and energizing, self tanning, soothing, as well as agents to improve elasticity and skin barrier and/or UV-filter substances. The topical cosmetic preparations can also contain usual cosmetic adjuvants and additives, such as preservatives/antioxidants, fatty substances/oils, water, organic solvents, silicones, thickeners, softeners, emulsifiers, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, antifoaming agents, pigments or nanopigments, e.g. those suited for providing a photoprotective effect by physically blocking out ultraviolet radiation, or any other ingredients usually formulated into cosmetic compositions. Such cosmetic ingredients commonly used in the skin care industry, which are suitable for use in the topical preparations of the present invention are e.g. described in the CTFA Cosmetic Ingredient Handbook, Second Edition (1992) without being limited thereto.

The usual cosmetic adjuvants and additives such as e.g. emulsifiers, thickeners, surface active ingredients and film formers can show synergistic effects which can be determined by the expert in the field with normal trials, or with the usual considerations regarding the formulation of cosmetic composition.

The necessary amounts can, based on the desired product, easily be determined by the skilled person. The cosmetically active ingredients useful herein can in some instances provide more than one benefit or operate via more than one mode of action.

If nothing else is stated, the carrier, excipients, additives, diluents, adjuvant and additives etc. mentioned in the following are in particular suitable for topical preparations according to the present invention.

The following examples are provided to further illustrate the invention. These examples are illustrative only and are not intended to limit the scope of the invention in any way.

EXAMPLE 1

Stability of $H_{29}C_{14}$—NH—CO-Dab-Val-Dab-OH

Solutions of 127 mmol/kg $H_{29}C_{14}$—NH—CO-Dab-Val-Dab-OH in a Glycerin water mixture (~2.3:1) containing salt concentrations of 382 mmol/kg have been prepared, distributed to 3 g per 10 ml glass vial and stored at 40° C. and 25° C. After various times, samples have been analyzed for their peptide content with analytical HPLC. The results have been normalized to the content at the preparation time to 100%.

TABLE 1 normalized peptide content in the presence of 3 eq. of salt after storage at 40° C.

|  | No salt | LiCl | $MgCl_2$ | $CaCl_2$ | $ZnCl_2$ |
|---|---|---|---|---|---|
| $t_0$ | 100.0 | 100.0 | 100.0 | 100.0 | 100.0 |
| 1 Month | 106.2 | 93.1 | 93.7 | 92.2 | 88.5 |
| 2 Month | 91.7 | 95.3 | 96.5 | 96.9 | 93.5 |
| 3 Month | 18.9 | 99.8 | 100.0 | 101.1 | 98.7 |
| 4 Month | 11.5 | 96.4 | 94.9 | 95.4 | 96.5 |
| 5 Month | 10.1 | 90.7 | 89.7 | 89.0 | 88.1 |
| 6 Month | n.d. | 87.6 | 90.7 | 88.9 | 92.3 |

EXAMPLE 2

Stability of Palm-Lys-Val-Lys-OH (SEQ ID NO:2)

Solutions of 119 mmol/kg Palm-Lys-Val-Lys-OH (SEQ ID NO:2) in Glycerin water mixture (~2.3:1) containing salt concentrations of one or three equivalents as indicated below have been prepared, distributed to 3 g per 10 ml glass vial and stored at 40° C. After various times, samples have been analyzed for their peptide content with analytical HPLC. The results have been normalized to the content at the preparation time to 100%.

TABLE 2 normalized peptide content in presence of various eq. salt after storage at 40° C.

|  | No salt | 3 eq $MgCl_2$ | 1 eq $MgCl_2$ | 3 eq NaCl | 3 eq LiCl |
|---|---|---|---|---|---|
| $t_0$ | 100.0 | 100.0 | 100.0 | 100.0 | 100.0 |
| 1 Month | 76.4 | 87.4 | 81.4 | 82.0 | 83.6 |

EXAMPLE 3

Stability of Palm-Lys-Val-Dab-OH (SEQ ID NO:5)

Solutions of 246 mmol/kg Palm-Lys-Val-Dab-OH (SEQ ID NO:5) in Glycerin water mixture (~2.3:1) containing salt concentrations of one or three equivalents as indicated below have been prepared, distributed to 3 g per 10 ml glass vial and stored at 40° C. After various times, samples have been analyzed for their peptide content with analytical HPLC. The results have been normalized to the content at the preparation time to 100%.

TABLE 3 normalized peptide content in presence of various eq. salt after storage at 40° C.

|  | No salt | 3 eq $MgCl_2$ | 1 eq $MgCl_2$ | 3 eq NaCl | 3 eq LiCl |
|---|---|---|---|---|---|
| $t_0$ | 100.0 | 100.0 | 100.0 | 100.0 | 100.0 |
| 1 Month | 44.2 | 70.5 | 71.7 | 75.7 | 75.9 |

The invention claimed is:

1. A method to reduce the adhesion of a peptide with 3-5 amino acids substituted with a saturated or unsaturated linear or branched chain hydrocarbon groups containing 8 to 20 carbon atoms, wherein said hydrocarbon group is connected thereto via an ester, amide, N-alkyl, N-alkenyl, sulfonyl, urethane or urea linkage to a surface, said method comprising combining said peptide with a water soluble salt of Mg, Ca, Zn and/ or Li.

2. The method of claim 1 wherein the peptide and water soluble salt are combined in an amount of 0.001-12.5 wt.-% peptide, and 0.00001-2 wt.-% water soluble salt, in a composition additionally comprising 10-95 wt.-%, of at least one water-soluble polyol containing 2 to 10 carbon atoms and 2 to 7 hydroxyl groups selected from the group consisting of ethylene glycol, 1,2-propylene glycol, 1,4-butylene glycol, glycerine, erythrit (meso-1,2,3,4-Butantetrol), sorbit, mannit, methylglucoside, diglycerine, triglycerine and pentaerythrit, and 10-90 wt.-%, of water wherein the total amount of ingredients of the composition sums up to 100 wt.%.

3. The method of claim 1 wherein the peptide and water soluble salt are combined in an amount of 0.01-2 wt.-% peptide, and 0.01-0.5 wt.-% water soluble salt, in a composition additionally comprising 40-80 wt.-% of at least one water-soluble polyol containing 2 to 10 carbon atoms and 2 to 7 hydroxyl groups selected from the group consisting of ethylene glycol, 1,2-propylene glycol, 1,4-butylene glycol, glycerine, erythrit (meso-1,2,3,4-Butantetrol), sorbit, mannit, methylglucoside, diglycerine, triglycerine and/ or pentaerythrit, and 20-50 wt.-% of water, wherein the total amount of ingredients of the composition sums up to 100 wt.-%.

4. The method of claim 1 wherein the peptide and water soluble salt are combined in an amount of 0.1-0.5 wt.-% peptide, and 0.02-0.01 wt.-% water soluble salt, in a composition additionally comprising 50-70 wt.-% of at least one water-soluble polyol containing 2 to 10 carbon atoms and 2 to 7 hydroxyl groups selected from the group consisting of ethylene glycol, 1,2-propylene glycol, 1,4-butylene glycol, glycerine, erythrit (meso-1,2,3,4-Butantetrol), sorbit, mannit, methylglucoside, diglycerine, triglycerine and/ or pentaerythrit, and 25-35 wt.-% of water, wherein the total amount of ingredients of the composition sums up to 100 wt.-%.

5. The method of claim 2, wherein the composition further comprising a cosmetically acceptable thickener and/ or a cosmetically acceptable tenside.

6. The method of claim 3, wherein the composition further comprising a cosmetically acceptable thickener and/ or a cosmetically acceptable tenside.

7. The method of claim 4, wherein the composition further comprising a cosmetically acceptable thickener and/ or a cosmetically acceptable tenside.

8. The method of claim 1, wherein the peptide is selected from Palm-Lys-Val-Lys-OH, Palm-Lys-Val-Dab-OH, Palm-Lys-Val-Dab-Thr-OH and/ or $C_{14}H_{29}$—NH—CO-Dab-Val-Dab-OH.

9. The method of claim 2, wherein the peptide is selected from Palm-Lys-Val-Lys-OH, Palm-Lys-Val-Dab-OH, Palm-Lys-Val-Dab-Thr-OH and/ or $C_{14}H_{29}$—NH—CO-Dab-Val-Dab-OH.

10. The method of claim 3, wherein the peptide is selected from Palm-Lys-Val-Lys-OH, Palm-Lys-Val-Dab-OH, Palm-Lys-Val-Dab-Thr-OH and/ or $C_{14}H_{29}$—NH—CO-Dab-Val-Dab-OH.

11. The method of claim 4, wherein the peptide is selected from Palm-Lys-Val-Lys-OH, Palm-Lys-Val-Dab-OH, Palm-Lys-Val-Dab-Thr-OH and/ or $C_{14}H_{29}$—NH—CO-Dab-Val-Dab-OH.

12. The method according to claim 1 wherein the water soluble salt is $MgCl_2$.

13. The method according to claim 2 wherein the water soluble salt is $MgCl_2$.

14. The method according to claim 3 wherein the water soluble salt is $MgCl_2$.

15. The method according to claim 4 wherein the water soluble salt is $MgCl_2$.

16. The method according to claim 2 wherein the at least one water-soluble polyol containing 2 to 10 carbon atoms and 2 to 7 hydroxyl groups is selected from glycerine, 1,2-propylene glycol and/ or 1,4-butylene glycol.

17. The method according to claim 3 wherein the at least one water-soluble polyol containing 2 to 10 carbon atoms and 2 to 7 hydroxyl groups is selected from glycerine, 1,2-propylene glycol and/ or 1,4-butylene glycol.

18. The method according to claim 4 wherein the at least one water-soluble polyol containing 2 to 10 carbon atoms and 2 to 7 hydroxyl groups is selected from glycerine, 1,2-propylene glycol and/ or 1,4-butylene glycol.

19. The method according to claim 1 wherein the surface is a container surface.

20. The method according to claim 2 wherein the surface is a container surface.

21. The method according to claim 3 wherein the surface is a container surface.

22. The method according to claim 4 wherein the surface is a container surface.

23. The method of claim 2, wherein the composition is a topical preparation comprising a cosmetically acceptable carrier.

24. The method of claim 3, wherein the composition is a topical preparation comprising a cosmetically acceptable carrier.

25. The method of claim 4, wherein the composition is a topical preparation comprising a cosmetically acceptable carrier.

26. The method of claim 2 wherein the peptide is combined in an amount of 0.01-2 wt.-%.

27. The method of claim 2 wherein the peptide is combined in an amount of 0.1-0.5 wt.%.

* * * * *